(12) United States Patent
Isserow et al.

(10) Patent No.: US 10,583,307 B2
(45) Date of Patent: Mar. 10, 2020

(54) HEATING DEVICE AND METHOD OF USE

(71) Applicants: Jonathan Isserow, Basking Ridge, NJ (US); Laura Isserow, Basking Ridge, NJ (US)

(72) Inventors: Jonathan Isserow, Basking Ridge, NJ (US); Laura Isserow, Basking Ridge, NJ (US)

(73) Assignee: TRANSQTRONICS, LLC., Wilmington, DE (US)

( * ) Notice: Subject to any disclaimer, the term of this patent is extended or adjusted under 35 U.S.C. 154(b) by 0 days.

(21) Appl. No.: 14/747,523

(22) Filed: Jun. 23, 2015

(65) Prior Publication Data

US 2015/0290028 A1    Oct. 15, 2015

Related U.S. Application Data

(63) Continuation-in-part of application No. 14/106,198, filed on Dec. 13, 2013, which is a
(Continued)

(51) Int. Cl.
*A61F 7/00* (2006.01)
*A61N 5/06* (2006.01)
(Continued)

(52) U.S. Cl.
CPC .......... *A61N 5/0616* (2013.01); *A61B 5/1491* (2013.01); *A61B 5/4836* (2013.01);
(Continued)

(58) Field of Classification Search
CPC ....... A61N 5/0616; A61N 5/062; A61F 7/007; A61F 2007/0233
See application file for complete search history.

(56) References Cited

U.S. PATENT DOCUMENTS 4,930,317 A * 6/1990 Klein ................. A61F 7/00
                                                        62/259.3
5,653,741 A * 8/1997 Grant ................. A61F 7/007
                                                        607/114
(Continued)

OTHER PUBLICATIONS

Wong RF, Kumar S, Bohra A, et al., "Systemic warming before, during, and after major abdominal surgery reduced postoperative complications more than warming during surgery only", 2007, Evidence Based Nursing, vol. 10, Issue 4, doi: 10.1136/ebn.10.4.114.*

(Continued)

*Primary Examiner* — Kaitlyn E Smith
*Assistant Examiner* — Yasamin Ekrami
(74) *Attorney, Agent, or Firm* — Gearhart Law LLC

(57) ABSTRACT

The present disclosure describes a treatment device having a heat source, a power source, a heat applicator and a lighting mechanism. The power source includes at least one battery having superior properties such as prolonged electricity production and prompt recharging. The heat applicator includes a heat conductive layer made from nanofibers, providing highly efficient heat distribution to the targeted regions. The lighting mechanism employs light emitting nano fibers to treat targeted regions. The power source provides energy to the light source, which generates light so that the applicator may distribute to an injury site or wound bed of a user. The heat source may be an exothermic chemical reaction designed to last for several hours supplying heat to the treatment device or an electronically produced heat. The treatment device further comprises a plurality of electrodes for electrical stimulation treatment.

22 Claims, 2 Drawing Sheets

Related U.S. Application Data continuation-in-part of application No. 14/081,110, filed on Nov. 15, 2013, now Pat. No. 9,675,817, which is a continuation-in-part of application No. 13/940,307, filed on Jul. 12, 2013, now Pat. No. 9,636,521, application No. 14/747,523, which is a continuation-in-part of application No. 13/747,584, filed on Jan. 23, 2013, now Pat. No. 10,010,445.

(51) Int. Cl.

| | | |
|---|---|---|
| *A61B 5/00* | (2006.01) | |
| *A61N 1/36* | (2006.01) | |
| *A61F 7/03* | (2006.01) | |
| *A61N 1/04* | (2006.01) | |
| *A61B 5/1491* | (2006.01) | |
| *A61F 7/02* | (2006.01) | |
| *A61B 5/145* | (2006.01) | |
| *A61B 5/01* | (2006.01) | |

(52) U.S. Cl.
CPC .............. *A61B 5/683* (2013.01); *A61F 7/007* (2013.01); *A61F 7/03* (2013.01); *A61F 7/034* (2013.01); *A61N 1/0452* (2013.01); *A61N 1/0456* (2013.01); *A61N 1/0492* (2013.01); *A61N 1/36021* (2013.01); *A61B 5/0022* (2013.01); *A61B 5/01* (2013.01); *A61B 5/145* (2013.01); *A61B 5/14507* (2013.01); *A61F 2007/0002* (2013.01); *A61F 2007/0029* (2013.01); *A61F 2007/0037* (2013.01); *A61F 2007/0039* (2013.01); *A61F 2007/0046* (2013.01); *A61F 2007/0052* (2013.01); *A61F 2007/0071* (2013.01); *A61F 2007/0078* (2013.01); *A61F 2007/0093* (2013.01); *A61F 2007/0094* (2013.01); *A61F 2007/0225* (2013.01); *A61F 2007/0226* (2013.01); *A61F 2007/0233* (2013.01); *A61F 2007/0234* (2013.01); *A61F 2007/0236* (2013.01); *A61F 2007/0261* (2013.01); *A61N 5/062* (2013.01); *A61N 5/0624* (2013.01); *A61N 2005/0645* (2013.01); *A61N 2005/0647* (2013.01)

(56) References Cited

U.S. PATENT DOCUMENTS

| | | | | |
|---|---|---|---|---|
| 5,658,583 | A * | 8/1997 | Zhang | A61F 7/034 424/402 |
| 6,567,696 | B2 * | 5/2003 | Voznesensky | A61F 7/007 607/108 |
| 7,503,927 | B1 * | 3/2009 | Vetanze | A61N 1/0408 607/115 |
| 8,133,264 | B1 * | 3/2012 | LaFontaine | A61F 7/007 2/125 |
| 2002/0026226 | A1 * | 2/2002 | Ein | A61F 7/007 607/108 |
| 2005/0028806 | A1 * | 2/2005 | Kumamoto | A61F 7/034 126/263.02 |
| 2006/0142816 | A1 * | 6/2006 | Fruitman | A61F 7/02 607/48 |
| 2006/0195168 | A1 * | 8/2006 | Dunbar | A61F 7/007 607/108 |
| 2008/0046047 | A1 * | 2/2008 | Jacobs | A61F 7/007 607/108 |
| 2008/0170982 | A1 * | 7/2008 | Zhang | B82Y 10/00 423/447.3 |
| 2008/0188915 | A1 * | 8/2008 | Mills | A61F 7/007 607/112 |
| 2011/0201984 | A1 | 8/2011 | Dubrow et al. | |
| 2011/0224584 | A1 | 9/2011 | Pryor et al. | |
| 2011/0309774 | A1 | 12/2011 | Peng et al. | |
| 2014/0031748 | A1 * | 1/2014 | Usui | A61F 7/03 604/113 |
| 2014/0364778 | A1 * | 12/2014 | Leftly | A61N 5/0613 601/18 |

OTHER PUBLICATIONS

Wagner, V. D. Effect of a preoperative warming intervention on the acute phase response of surgical stress (Order No. 3306842). Oct. 31, 2007, Available from ProQuest Central; ProQuest Dissertations & Theses Global. (304819228). Retrieved from http://search.proquest.com/docview/304819228?accountid=14753.*

State Intellectual Property Office of China; First Office Action; CN Application No. 201480016608.1; dated Aug. 9, 2016; China.

State Intellectual Property Office of China; Second Office Action; CN Application No. 201480016608.1; dated Jun. 19, 2017; China.

* cited by examiner

HEATING DEVICE AND METHOD OF USE

CLAIM OF PRIORITY

This application is a continuation in part of U.S. application Ser. No. 14/106,198 filed one Dec. 13, 2013 which is a continuation in part of U.S. application Ser. No. 14/081,110 filed on Nov. 15, 2013 which is a continuation in part of U.S. application Ser. No. 13/940,307 filed on Jul. 12, 2013, the contents of said applications being fully incorporated by reference in their entirety. This application is also a continuation in part of U.S. application Ser. No. 13/747,584 filed on Jan. 23, 2013, now U.S. Pat. No. 10,010,445 the contents of which is also herein fully incorporated by reference in its entirety.

FIELD OF THE EMBODIMENTS

The present invention and its embodiments relate to a wound and/or skin care treatment device and related methods of use. In particular, by using heating, nanotechnology, lighting, and electrical stimulation, the present invention relates to a device and method(s) that may be used for treatment of a wound, injury, skin infection such as acne, ailment, or disease, as well as pre-treatment and post-treatment to prevent wound infections prior to surgery and maintaining normothermia during surgery.

BACKGROUND OF THE EMBODIMENTS

Many kinds of diseases and accidents may cause harm to the human body, the resulting in pain, wounds, infections, and injuries require both swift and continuous treatments. The treatment of such wounds/injuries has been a crucial part of healthcare. Various methods and devices have been developed to improve the quality of care that may be provided in such treatments and the healing process. Among these approaches are temperature alternation techniques, such as the application of heat or coldness by different sources.

Application of heat, or coldness, or alternating temperature changes have been widely used in the treatment of wound, infection, pain, and injury for a very long time. In addition, the heating treatment may also prevent cutaneous/skin infections as well as preventing skin infection pre-operatively. Heating treatments such as heat pads are believed to cause the dilation of blood vessels, facilitate perfusion to the target tissues and cycling of blood, and sterilize the targeting area. Cold treatments such as ice pads reduce swelling and are used in pain management following injury.

The temperature altering treatments, especially the application of heat, are widely in use but there are still a number of general shortcomings. Wound healing involves a complex series of biochemical events, and is traditionally managed with low tech options. For example, previous heat applicators are generally bulky and difficult to fit onto small wounds or injuries at locations that are hard to access. Perioperative heat treatment, known to significantly reduce post-operative wound infection, is currently not practically available because of a limitation in available devices that are portable and do not require bulky hardware for each individual patient to facilitate treatment. There is a distinct need for an easy to use portable inexpensive bandage device that can be applied perioperitvely to all patients that is not limited by the resource of fixed, expensive hardware. In addition, the regular heating applicators are not long lasting, requiring frequent change of the applicator. Thirdly, some of the heat applicators are hard to reheat. The ability to provide consistent thermoregulation is critical to the prevention of infection as fluxes in temperature (i.e. too hot or not hot enough) can have an adverse outcome in patient management.

In general, the existing heating application treatment devices are low in efficiency and high in waste of energy. These treatment devices cannot keep up with the development of new problems, such as the escalating crisis of multi-drug resistant infections including Methicillin-resistant *Staphylococcus aureus* (MRSA). The medical literature demonstrates significant reduction in post-operative wound infection in patients who received local warming prior to surgery for a 30 minute period with reduction in rates of wound infection from 14% in non-warmed patients to 5% in warmed patients (greater than 60% reduction in wound infection). It is critical that an easy to use device with thermoregulatory control be available to all patients undergoing surgery particularly in light of the escalating crisis of multi-drug resistant infections including Methicillin-resistant *Staphylococcus aureus* (MRSA). Further, theranostic and diagnostic sensors can be implemented to aid in wound care optimization for both acute and chronic wounds. This optimization can reduce hospital stay times, reduce costs, and prevent further infection(s). Therefore, the development of new technology is desirable and the current invention serves as a powerful alternative to the previous devices.

The application of light to the human body is the basis for phototherapy. These therapies have been used in the treatments of many ailments such as cancer, acne, and psoriasis. Similar to temperature therapies, the application of some types of lights, such as lasers, helps to promote circulation. Photodynamic therapies are also used. This form of phototherapy uses a non-toxic, non-reactive substance that when exposed to select wavelengths of lighting becomes toxic and attacks the targeted cells. This is instrumental in being able to target a particular cell or area and have the advantage of leaving surrounding tissue unharmed. Light related therapy can kill many bacteria, fungi, and viruses.

However, the increasingly popular phototherapies have a number of general shortcomings as well. The current phototherapeutic models on the market for treating acne have a limited functionality, are small, hand held, and effective for only treating one small skin area at a time. Depending on the person, this can end up taking an inordinate amount of time. There are larger models on the market, however, these models are also not form fitting and require a user to simply hold the device to the affected area for the prescribed amount of time. Thus, the user must remain in a fixed position for upwards of one hour and then change the position of the device to treat another area.

Nanotechnology stands at the vanguard of integrating science and engineering and it has undergone significant progress in recent years. By using materials having nanometer level dimensions and special physical characteristics, nanotechnology has proven to be a promising field of innovation. In particular, a number of improvements in nanotechnology using nanofibers, nanotubes, and nano-particles have enabled the production of batteries that provide higher energy density, last longer, and/or recharge faster. In addition, nanofibers have been shown to be applicable in a number of disciplines such as material science, molecular biology, and medical sciences. Nevertheless, the use of nanofibers and nanotechnology batteries in medical devices, in particular treatment devices, has been scanty and leaves much to be desired. The current invention addresses the aforementioned needs.

REVIEW OF RELATED TECHNOLOGY

US Patent Application 2008/0023394 pertains to a medical filter material comprising a dispersion of nanofibers of thermoplastic polymer having a number average diameter of 1 to 500 nm wherein the ratio of single fibers with a diameter of more than 500 nm and 1 nm or less is 3% or less in terms of weight ratio. Further, there are provided, utilizing the medical filter material, an extracorporeal circulation column and a blood filter. Through the employment of nanofibers small in fiber diameter dispersion, high in strength and high in productivity, there can be provided a medical filter material excellent in hemadsorption performance and protein adsorption performance. Through packing with this medical filter material, there can be provided high-performance extracorporeal circulation column and blood filter.

US Patent Application 2008/0069905 pertains to a therapeutic treatment device comprising a compound comprising a drug and a nitric oxide (NO) eluting polymer arranged to contact a treatment site in or on a body. The device is acting as a booster for drug eluting patches, e.g. pharmaceuticals, vitamins, nicotine, nitroglycerin, whereby with advantage two therapeutic treatments, of significant value, are combined in one treatment. A synergetic effect is achieved by such devices because NO that is eluted from the device boosts the effect of the drug, as the treatment site is more susceptible to said drug by the effect of the eluted NO.

Various devices are known in the art. Nevertheless, their structures are distinctively different from the current invention. Moreover, the other inventions fail to address all of the problems solved by the invention described herein. The present invention is a multifunctional, multipurpose cutaneous platform that is worn on the skin. The device generates multiple stimuli including but not limited to thermoregulation, phototherapy, electrical, radio frequency, chemical, and pharmaceutical. One embodiment of this invention is illustrated in the accompanying drawings and will be described in more detail herein below.

SUMMARY OF THE EMBODIMENTS

The present invention is a treatment device that is intended to function in both a research capacity by activating neural pathways and as a therapeutic modality in translating and inducing electrical signals specific to diseased and healthy states. The device provides a critical tool for researchers and patients alike. The treatment device disclosed herein utilizes, amongst other materials, nanotechnology in applications for wound therapy, thermotherapy, phototherapy, photodynamic therapy, electrical stimulation therapy, pain management, drug delivery, timed therapeutic release, local and remote wound monitoring, remote therapeutic delivery applications, electrical/chemical stimulation or modulation, radio frequency applications, and multiple dermatological applications. The various applications may be utilized remotely through wireless smart technology platforms.

In one embodiment there is a treatment device having a chemical heat source, wherein the chemical heat source can produce a temperature in the range of about −10° C. to about 50° C.; a heat applicator connected to the chemical heat source; the heat applicator having a heat application layer having an application surface and a heat receiving surface, and a heat conductive layer having a front side and a back side, wherein the heat conductive layer is made of nanofibers extensively affixed to the heating receiving surface of the heat application layer; a plurality of electrodes integrated with the heat application layer, wherein the electrodes are coupled to the power source providing a mechanism for neuromuscular stimulation; a power source connected to the treatment device, empowering the light source, wherein the power source is at least one battery, a lighting mechanism interwoven into the heat application layer; and a control mechanism for changing the operative state of the lighting mechanism.

In the treatment device, the power source and the heat source are integrated into a heat generating body. The heat generating body is directly attached to the heat applicator. The power source is further controlled by a control mechanism which is capable of turning some of the components of the treatment device on, off, or adjusting the output of the power source. For example, the treatment device may provide for the inclusion of a lighting mechanism in the form of a plurality of light emitting nano fibers. The power source or control mechanism could turn the lighting mechanism on, off, or adjust the intensity of the light emitted by the lighting mechanism. The power source can also make adjustments to the electrical stimulation system as well as change the operative state of the electrodes. The chemical heat source is a self-contained exothermic chemical reaction involving iron, which could include, for example, iron filings and other components to a contained apparatus with access to oxygen. In order to provide this access (breathability) of the device thin porous materials are used to ensure proper transfer of heat and gases.

The treatment device generally takes the form of a cutaneous patch that can be applied to the body of the patient or user. Further, the device may be a stocking, sleeve, cap, mask, or the like. The device has a non-sticky layer on the heat application surface that prevents the treatment device from sticking to the user. The treatment device is generally used in the treatment of skin conditions, wounds, and injuries through heat, electrical stimulation, and photodynamic therapies. However, the principles may be applied to other uses such as general warming, lighting, or treatment of pests such as lice and bedbugs and house dust mites.

In some embodiments, the heat conductive layer comprises nanofibers woven or unwoven but pressed into a layer that efficiently and extensively transfers heat to the heat application layer. Many specific nanofibers, nanofilaments or nanotubules may be used in the heat conductive layer. The nanofibers could be sheets, mats, yarns, or tapes and the particular configuration can be selected to best suit the intended usage of the treatment device. In some instances, this nanofiber material may not be required for usage and other heat conductive metals, alloys, or other material or any combination thereof can be used to conduct and/or distribute heat or current. Preferably, the lighting mechanism comprises light emitting nanofibers. For clarity purposes, the term nanofiber is used to generally cover all the nanofibers, nanofilaments, nanotubules, and other fibrous materials having diameters preferably between 0.5 nm and 1 µm. Additionally, the materials may be of a micro origin of about 100 nm to 100 µm in diameter. The nano particles used in the present invention may be theranostic nano particles capable of therapeutic and diagnostic capabilities.

The power source is preferably a nanotechnology battery that possesses certain superior properties compared with conventional lithium batteries but may also comprise other chemical mechanisms. In some instances, other batteries and battery technologies may be employed including non-nano batteries. The power source may produce higher energy density. The power source may last longer than conventional batteries. The power may also be charged and recharged promptly. In particular, nanotechnology has been used to produce "supercapacitors" that may be incorporated in rechargeable batteries. Preferably, the current treatment device employs such a supercapacitor battery allowing quick recharges.

In another aspect of the present invention there is a method of medical treatment comprising the steps of: providing a medical treatment device, the medical treatment device comprising, a heat source, wherein the heat source is capable of producing a temperature in the range of about $-10°$ C. to about $50°$ C.; a heat applicator connected to the heat source; the heat applicator comprising, a heat application layer having an application surface and a heat receiving surface, and a heat conductive layer having a front side and a back side, wherein the heat conductive layer is extensively affixed to the heating receiving surface of the heat application layer; a power source connected to the heat source, wherein the power source is at least one battery; applying the medical treatment device to at least one patient for a predetermined time frame before the at least one patient undergoes at least one medical procedure.

In yet another embodiment there is a method of medical treatment comprising the steps of: providing a medical treatment device, the medical treatment device comprising, a heat source, wherein the heat source is capable of producing a temperature in the range of about $-10°$ C. to about $50°$ C.; a heat applicator connected to the heat source; the heat applicator comprising, a heat application layer having an application surface and a heat receiving surface, and a heat conductive layer having a front side and a back side, wherein the heat conductive layer is extensively affixed to the heating receiving surface of the heat application layer; a power source connected to the heat source, wherein the power source is at least one battery; applying the medical treatment device to at least one patient for a predetermined time frame before the at least one patient undergoes at least one medical procedure; applying the medical treatment device to the at least one patient after the at least one patient has undergone at least one medical procedure for a second predetermined time frame; and applying the medical treatment device to the at least one patient for at least one subsequent timed interval, wherein each subsequent timed interval is the same or different in duration as any other timed interval.

Using the device described above, the user of the device may cause thermal and luminary alternations to the injury site or wound bed, allowing faster and more complete recovery. In particular, the device may be used to apply heat to the injury site or wound bed. The device may also be used to prevent and treat infections such as bacterial infections that are susceptible to increased temperature. The specific applications of the device are extensive. Additionally, the functional mechanism of the device may vary as well.

The device may employ a nanofiber/battery platform, wherein the battery powers the device and uses nanofibers to properly distribute the generated heat. In lieu of a battery, the device may operate on an electrical platform using a conventional 15 A/125V or 20 A/125V AC power supply (i.e. wall outlet socket). In some embodiments, the heat source is embodied as a light source (i.e. infrared), silicon heat source, flexible heat source, or ceramic heat source. In some embodiments, for proper functioning, the heat source may require an operating voltage of about 12V to about 250V and more preferably about 90V to about 125V. In some embodiments, the heat source uses about 80 W and about 160 mA to about 20 A and more preferably about 0.6 A. Operating frequencies may range from about 40 Hz to about 80 Hz and more preferably about 50 Hz to about 60 Hz. If wireless transmission means are to be used in the device, the electric field strength may be about 1 V/m to about 10 V/m and more preferably about 3 V/m. Combinations of characteristics as described above may be used as necessary and in some instances may be apparent to those skilled in the art.

Further, the device may operate with no attached power source and derive its heating qualities from chemical reactions occurring within the confines of the device. Such exothermic reactions would be suitable to supply the necessary heat for at least 8-12 hours and possibly more. The device may also employ any combination of heat production (battery, electrical, chemical) in conjunction with one another. In such a case, the various methodologies may distinct roles. For example, the battery of the device could power the lighting mechanism, while the chemically produced heat could supply the heating quality of the same device. The heating mechanism(s) may also be used and be sufficient for use without the inclusion of the nanofiber material.

The treatment device may further comprise a control mechanism connected to the power source. The device can be remotely programmable utilizing Bluetooth®/smart phone technology so that a patient and/or physician could program the device remotely or wirelessly for certain predetermined light cycles or other functionality such as electrical stimulation and heating cycles. The device could also provide real time feedback in terms of patient data based on a variety of chemical or biological sensors including but not limited to temperature, pH, wound exudates, microbial levels and/or presence as well as visual data such a spectroscopic and various other imaging techniques.

In general, the present invention succeeds in conferring the following, and others not mentioned, desirable and useful benefits and objectives.

It is an object of the present invention to provide a treatment device that may be used to facilitate the healing of injuries, infections, acne, or wounds on humans and other subjects.

It is an object of the present invention to provide a treatment device that may cover the wound bed or injury site.

It is an object of the present invention to provide a treatment device that alters the temperature of a wound, infection or injury site.

It is an object of the present invention to provide a treatment device that applies heat to a wound or injury site.

It is an object of the present invention to provide a treatment device that is light and portable.

It is another object of the current invention to provide a treatment device that may be used for different kinds of wounds/infections/injuries and reduce in wound scarring.

It is another object of the current invention to provide a treatment device that may be used for wounds/injuries on different parts of a body, including musculoskeletal pain.

It is still another object of the current invention to provide a treatment device that is easily adjustable.

It is another object of the current invention to provide a treatment device that uses a supercapacitor battery that is easily rechargeable.

It is yet another object of the current invention to provide a treatment device that uses nanofibers for efficient heat conduction.

It is an object of the present invention to provide a treatment device that uses nanofibers for efficient heat conduction.

It is another object of the current invention to provide a treatment device that has an integrated body, while still allowing for the replacement or exchange of components including power sources.

It is yet another object of the current invention to provide a treatment device that is easy to use and easy to manufacture.

It is an object of the present invention to provide a treatment device that uses heat energy to treat vascular ailments such as poor circulation including peripheral vascular disease and diabetes.

It is an object of the present invention to provide a treatment device that functions as a hot/cold compress.

It is an object of the present invention to provide a treatment device that helps an individual to maintain a homeostatic temperature including maintaining normothermia and specific core temperature requirements for patients before, during, and after surgery.

It is an object of the present invention to provide a treatment device that uses light for the purpose of phototherapy and photodynamic therapies.

It is another object of the present invention to provide a treatment device that uses heat and/or light to facilitate the release of and/or increase absorption and efficacy of topical medicinal applications including creams, ointments, photodynamic agents and topical antibiotics and nano therapy particles.

It is another object of the present invention to provide a treatment device that uses light for the treatment of varying skin conditions including red, green, and blue light sources.

It is another objective of the present invention to provide a treatment device that uses bipolar radio frequency and/or light energies in the removal of hair.

It is another objective of the present invention to provide intense pulsed light, laser and other light applications with specific ability to regulate dosimetry and duration of therapy as well as location (area treated) during therapy.

It is another object of the present invention to provide a treatment device that uses transcranial low level laser therapy (LLLT) in the management of traumatic brain injury and stroke, pain, and symptoms related to medical conditions including rheumatoid arthritis, osteoarthritis, tendinopathy, and wound treatment.

It is an object of the present invention to provide a treatment device that can be inserted into orthopedic casts for reduced healing time and wound infection prevention and management.

It is an object of the present invention to provide a treatment device capable of providing early therapy for patient with a suspected stroke, where light therapy has applications in the management of cerebrovascular accident and traumatic brain injury.

It is an object of the present invention to provide a treatment device that can act as an advanced hot and cold compress for treating injuries and pain.

It is an object of the present invention to provide a treatment device that can be programmable directly and/or remotely utilizing Bluetooth®/smart phone technology so that a patient and/or physician could program the device remotely or wirelessly for certain predetermined cycles and functions. The device could also provide real time feedback in terms of data including physiological as well as visual data.

It is another objective of the present invention to provide a treatment device that can be used for menstrual pain management with heat therapy.

It is yet another object of the present invention to provide a treatment device for internal applications including the management of cervical conditions.

It is another object of the present invention to provide a treatment device that can utilize a nano generator whereby mechanical movement can harvest energy utilizing piezoelectric technology by converting energy from mechanical stresses into energy properties for lighting purposes.

It is another object of the present invention to provide a treatment device the can utilize nanophotonics/light-emitting nano fibers and/or Photoluminescent nano fibers, nanofibers and luminescent particles such as quantum dots (QDs).

It is another object of the present invention to provide a treatment device that facilitates light generation utilizing preferably nano components and is rechargeable and/or disposable.

It is another object of the present invention to provide a treatment device that micro components could be used if desired.

It is another object of the present invention to provide a treatment device that can be used for heat redistribution for computers, electronics, and air conditioners.

It is an object of the present invention to provide a treatment device that serves as a multifunctional, multipurpose cutaneous platform that can generate multiple stimuli including but not limited to thermoregulation, phototherapy, electrical, radio frequency, chemical, and pharmacological stimuli.

It is an object of the present invention to provide a treatment device that can be programmed to induce specific electronic signature(s) or other stimuli to bypass/remediate the aberrant neural signaling in diseases states.

It is an object of the present invention to provide a treatment device that affects the axon reflex pathways, including vasoconstriction and vasodilation, using electrical stimulation.

It is yet another object of the present invention to provide a treatment device that functions to aid in a better understanding of the neural mechanisms involved in specific neuropathic disorders and providing tailored therapeutic options including transcutaneous electrical stimuli.

It is another object of the present invention to provide a treatment device that records neural signaling of the peripheral nervous system including in disease and health states.

It is another object of the present invention to provide a treatment device that can be used to warm intravenous fluids.

It is another object of the present invention to provide a treatment device that provides thermoregulation of the male reproductive system to improve fertility.

It is another object of the present invention to provide a treatment device that uses phototherapy to restore or prevent hair loss.

It is another object of the present invention to provide a treatment device that uses radio frequency to induce hair loss.

It is yet another object of the present invention to provide a treatment device that utilizes photodynamic antimicrobial chemotherapy in treating localized wounds and/or infections.

DETAILED DESCRIPTION OF THE EMBODIMENTS

Figure 1:
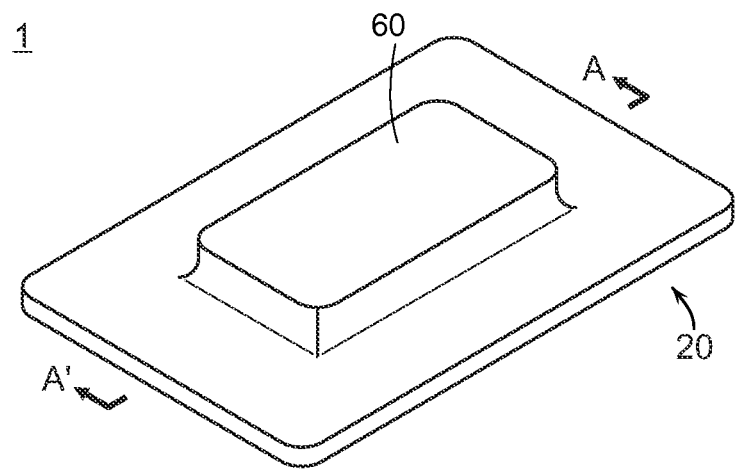
FIG. 1 shows a back perspective view of a treatment device embodying the current invention.

The preferred embodiments of the present invention will now be described with reference to the drawings. Identical elements in the various figures are identified, as far as possible, with the same reference numerals. Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto without deviating from the innovative concepts of the invention.

FIG. 1 shows a back perspective view of a treatment device embodying the current invention.

Figure 2:
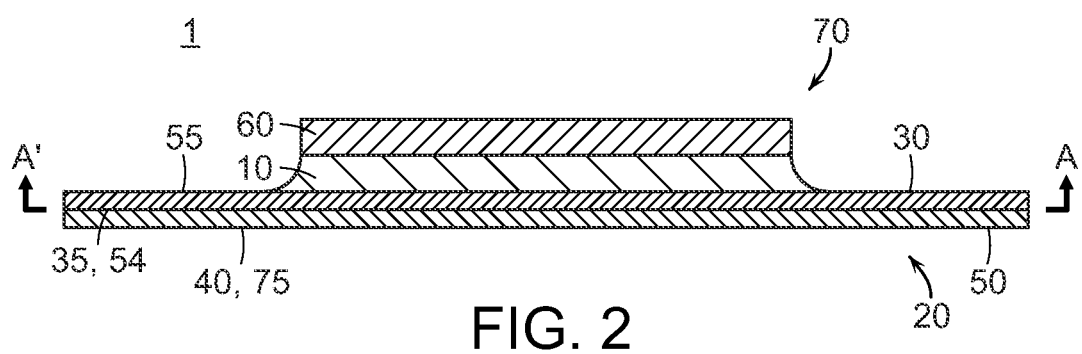
FIG. 2 shows a sectional view along plane A-A' of the treatment device shown in FIG. 1.

FIG. 2 shows a sectional view of the treatment device shown in FIG. 1, as indicated by markers A and A'. Shown in FIG. 2 is the treatment device 1 having a heat generating body 70 attached to a heat applicator 20. The heat generating body 70 comprises a heat source 10, which may be chemically or electrically based, and a power source 60. In addition, the heat applicator 20 comprises a heat application layer 50 and a heat conductive layer 30, wherein the heat application layer 50 has a heat receiving surface 35 and a heat application surface 40, and the heat conductive layer 30 has a front side 54 and a back side 55. The heat application surface 40 has a lighting mechanism 75. Preferably, this lighting mechanism 75 manifests itself as a light emitting nano fiber woven into the heat application surface 40. The front side 54 of the heat conductive layer 30 directly engages with the heat receiving surface 35 of the heat application layer 50. The heat application surface 40 is designed to engage exposed human wound beds or injury sites.

Figure 3:
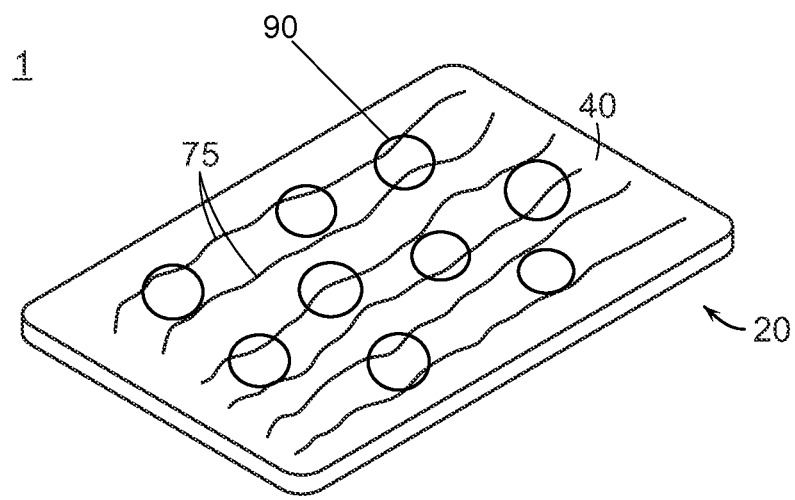
FIG. 3 shows a front perspective view of the treatment device.

FIG. 3 shows a front perspective view of the treatment device 1. Shown in FIG. 3 is the heat application surface 40 with the integrated lighting mechanism 75 of the heat application layer 50, which is part of the heat applicator 20.

Figure 4A:
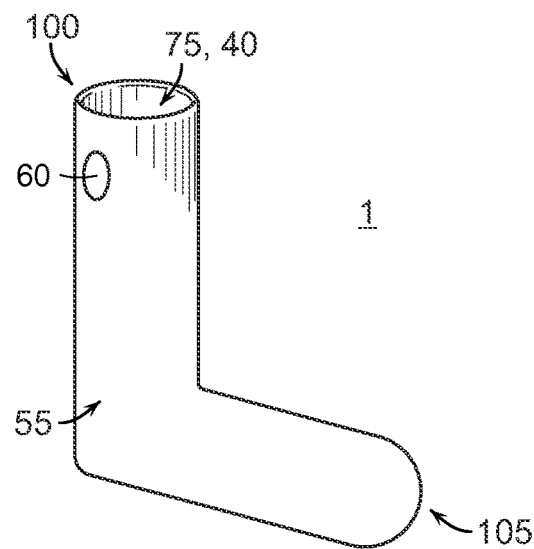
FIG. 4A shows an illustration of an alternate embodiment of the treatment device as an arm sleeve.

FIGS. 4A, 4B, 4C and 4D display alternate embodiments of the current invention. In FIG. 4A, the current invention is shown as a stocking for a leg. The individual slides their leg into the void 100 until their toes are resting comfortably in the terminal end 105 at the base of the device 1. The heat source 10 permeates the entire stocking providing even heating throughout the device 1. The stocking may include toe slots, similar to toe socks, rather than a uniform base. This would provide more surface area for the heat and light to treat.

Figure 4B:
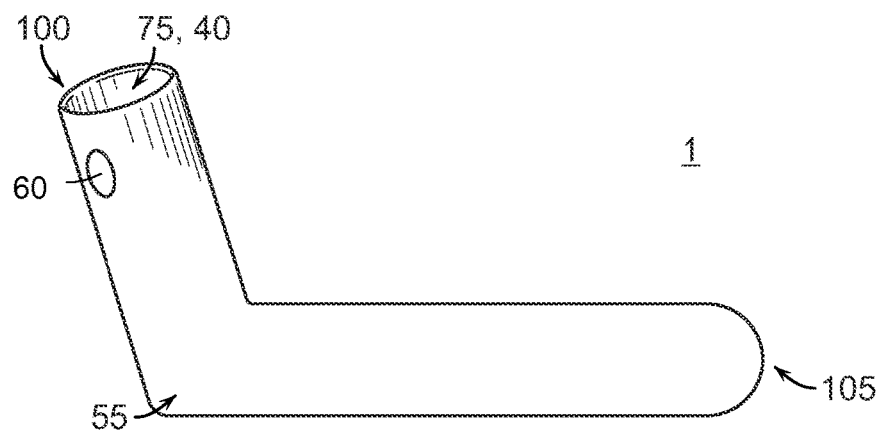
FIG. 4B shows an illustration of an alternate embodiment of the treatment device as a leg sleeve.

In FIG. 4B, the device 1 is shown as a stocking for an arm. Again, a user slides their arm into the void 100 and to the terminal end 105 at base of the stocking. The stocking may include finger slots, like a mitten, to provide an increased surface area for the heat and light to treat.

Alternatively, the device 1 comprising the stocking may be of differing sizes and have Velcro® hook and loop fastener, or another adhesive means, to wrap and secure the apparatus to the affected limb. The stocking may also have a preformed shape (to fit an extremity) with openings disposed at each end. Thus, this would be a more traditional sleeve rather than a stocking and provide a greater range of mobility. Such varying embodiments would be most beneficial to those that are afflicted by diabetes, vascular diseases, and the like. These individuals typically have poor circulation that sometimes requires amputation of the affected appendage.

The increased heat focused on these areas promotes increased blood flow and anti-inflammatory qualities, which, in turn, may aid in the prevention of such drastic measures from being taken. Additionally, the increased blood flow can increase nitric oxide (NO) production and delivery. Nitric oxide is a vasodilator and thus can have a synergetic effect along with the heat treatment. Thus, with the aid of this device 1 increased NO production can be done by taking advantage of physiological mechanisms rather than by employing expensive pharmaceuticals.

Figure 4C:
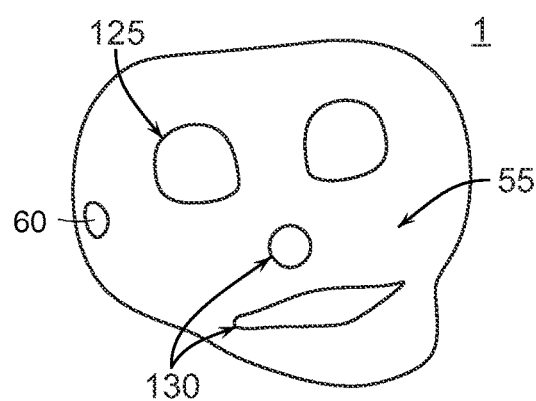
FIG. 4C shows an illustration of an alternate embodiment of the treatment device as a mask.

In FIG. 4C, the treatment device 1 takes the form of a mask. The mask has protective eye slits 125. These protective eye slits 125 remove heat and/or light from the area and protect the eye from any harm stemming from the treatments. The protective eye slits 125 may also have built-in protective coverings for the eyes, similar to goggles, to generally protect the eyes from harm related to usage of the device 1. The wavelengths typically used with the treatment of some skin ailments (blue and red) can damage the retina of the eye without proper protection. The mask also provides for breathing slits 130 as well to aid in the comfort of the wearer.

Figure 4D:
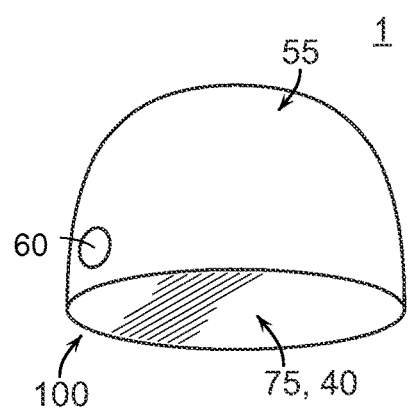
FIG. 4D shows an illustration of an alternate embodiment of the treatment device as a wearable cap.

In FIG. 4D, the treatment device 1 takes the form of a wearable cap or head covering. The cap may come in variable sizes or have the ability to conform to the user's head. The user puts the device 1 onto their head by placing their head in the void 100 until the top of their head touches the heat application surface 40. From there, the heat source 10 provides the heat desired by the user. This embodiment is key in fighting various afflictions centered on the head of the user. For instance, lice and bed bugs are both susceptible to heat. Heat treatments can be used to help rid an individual of these parasites.

The power source 60 of the current invention may employ any kind of electricity generating or storing devices. Preferably, the power source 60 here is a rechargeable battery using nanotechnology. For example, the nanotech battery may use silicon nanowires on a stainless steel substrate, providing upwards of 10 times the power density of conventional lithium ion batteries. Alternatively, the nanotech battery may use aligned carbon nanotubes on a substrate to establish the anode or cathode in a conventional battery, improving the power generating capacity by almost 10 fold.

More preferably, the power source is a battery utilizing nanotech supercapacitor technology, which can be recharged promptly. For instance, by using graphene on the surface of anodes to make lithium-ion batteries, the batteries may be recharged 10 times faster than common rechargeable batteries. The fast recharging nanotech batteries are particularly suitable as the power source 60 herein included in the current invention. With such designs, the treatment device may be used more widely in emergency situations because the initiation of treatment and alternation of devices may become more time-saving and efficient.

In other embodiments, the treatment device is connected to an external power source which also contains hardware, software, programming, and thermal controls for the monitoring and regulation of the device in use. In such an embodiment, the bulk of the functionality is separated from the heat application mechanism thereby allowing the device to be disposable and the tethered unit or external power source to be used with different patients and/or treatments.

In addition to the technologies described above, the power source 60 may also use other nanotechnology, such as but not limited to: lithium sulfur batteries (using carbon nanofibers encapsulating the sulfur in the cathode or using mesoporous carbon nanoparticles that embraces sulfur inside the nanopores of the cathodes), nanocomposite batteries (using cathodes made of a nanocomposite designed to increase the energy density of the Li-ion batteries), nanostructured lithium titanate battery having enhancing charge/discharge capability, fast charge/recharge batteries using silicon nanoparticles coating a titanium disilicide lattice, thermocells using nanotubes that generate electricity, electrical generator built with nanostructured material that can generate electrical power from the user's body motion such as walking, and ultracapacitor batteries using single atom thick graphene sheets, and any combinations of batteries and power sources thereof.

Besides incorporating nanotechnology batteries, the power source 60 may also utilize other readily available supplies of electricity. For example, the power source 60 may be a power cord and power plug that can be directly connected to a common alternating current electricity outlet. Alternatively, the power source 60 may be a regular battery or battery pack, either rechargeable or non-rechargeable. The battery may also be sufficiently thin and flexible such as the zinc based Zincpoly™ by Imprint Energy of Alameda, Calif. Other zinc based and other batteries may be used such as regular AAA zinc-carbon or alkaline batteries, or any other type or size that may fit the energy needs and/or physical accommodations of the current treatment device.

Alternatively, the power source 60 may be a nano generator. The nano generator may have a piezoelectric property that allows energy harvesting from mechanical stresses. Such an option would allow for the operation of the device 1 without a battery. However, it may be practical to employ a back-up battery in case of generator failure.

The heat source 10 is used to produce heat through a variety of mechanisms. In one instance, the heat source 10 is a natural chemical reaction, preferably the oxidization of iron. Alternatively, the heat source 10 may rely on electrical energy for manipulation of the heat source's 10 output. The design of the heat source 10 is generally known in the art and it may vary according to the characteristics and requirements of the user and the injury/wound/infection to be treated. The treatment device 1, in some embodiments, may utilize light, such as infrared light, as a heat source. In some embodiments, it is preferable that the light is far infrared light (FIR).

The heat source 10 (derived from chemical pathways) may include other compounds such as sodium thiosulfate, water, charcoal, sodium chloride, and sodium polyacrylate amongst others that are designed to regulate the speed of the reaction, the heat produced, and other necessary factors. Similar heat generating compositions can be found in the Hot Hands® chemical heat packs sold and distributed by Walk-Winn Plastics Co. of Little Rock, Ark. Typically exposure to air or by breaking internal compartments the chemicals are permitted to produce an exothermic reaction. Ideally, the heat source 10 will regulate the iron oxidation to produce heat reaching approximately 38° C. (about 100° F.) for about 8-12 hours.

The heat source 10 may be a separate structure from the power source 60, or on the alternative, a part of an integrated structure, such as a heat generating body 70, which also includes the power source 60. The heat source 10 may be located in a particular area of the treatment device 1 or the heat source 10 may exist throughout the device 1 providing heat. Alternatively, by using a solution of super saturated sodium acetate contained within an internal pouch, a reusable heat source may be generated. A metal disc contained within the pouch, that when flexed, causes the solution to solidify and heat to be generated. In still other embodiments, infrared heating may be employed by the treatment device 1. Depending on the choice of the heat source 10 and the methodology desired, radiant heating may be used as a form of non-contact heating of the wound and/or wound area.

The connection between the heat source 10 and the power source 60 may vary as well. In an alternative embodiment, the power source 60 is removably attached to the heat source 10, wherein the treatment device 1 still utilizes the generated heat without requiring light therapy, which is used to treat the wound bed or injury site, reducing the weight the treatment device and allowing the user of the treatment device to move around more freely. In another embodiment, the power source 60 may be connected to a plurality of heat sources 10 by long wires to ensure continued power supply to a number of treatment devices.

The electronically controlled heat source 10 may have a wider temperature range than when chemicals are used. Preferably, the heat source 10, in this instance, will be able to warm the device 1 to provide therapeutic heat treatment, as well as remove heat to provide a cold compress treatment. For example, the heat source 10 may be capable of producing temperatures in the range of about −30° C. to about 90° C. and more preferably from about −10° C. to about 50° C. This allows the treatment device 1 to have greater thermal regulation capabilities and can alternate between "hot" and "cold" treatments. This can further be enhanced by lining the inner walls of orthotic device (braces) with the treatment device 1. It can also be appreciated that chemical reactions can be used to create similar temperatures within the range, but rather will be limited to a narrow range rather than alternating between ends of the spectrum.

The heat applicator 20 is designed to apply the heat produced by the heat source 10 to the user of the treatment device. The heat applicator 20 in the current embodiment has a heat application layer 50 and a heat conductive layer 30. However, it should be noted that the heat application layer 50 and the heat conductive layer 30 may be a single layer integrated together and having both heat application and heat conducting capabilities. As to the embodiment shown in FIG. 2, the heat conductive layer 30 may be made from woven or unwoven nanofibers that are extensively affixed to the back side of the heat application layer 50. The nanofibers used in the heat conductive layer 30 may include but not limited to: inorganic nanofibers such as ceramic nanofibers made from titanium dioxide ($TiO_2$), silicon dioxide ($SiO_2$), zirconium dioxide ($ZrO_2$), aluminum oxide ($Al_2O_3$), lithium titanate ($Li_4Ti_5O_{12}$), and titanium nitride (TiN) or platinum (Pt), organic or polymer nanofibers such as but not limited to polystyrene, polyacrylonitrile, polycarbonate, PEO, PET and water-soluble polymer nanofibers, and bi-component nanofibers, and any combinations thereof.

Such inorganic nanofibers are typically produced via a conventional electrospinning technique which employs an electrical charge to a polymer solution to draw fine nano-sized (or micro) fibers from the liquid. Organic nanofibers such as carbon nanofibers are synthesized using a catalytic synthesis. Here, gas phased molecules are decomposed at high temperatures and the carbon is deposited on a transition metal catalyst. Generally, this involves a series of separate stages such as gas decomposition, carbon deposition, fiber growth, fiber thickening, graphitization, and purification of the now hollow fibers. Such nanofibers as described herein may be similar to those available from or developed by SNS Nano Fiber Technology, LLC of Hudson, Ohio. The key property of the nanofibers making up the heat conductive layer 30 is that the nanofibers are capable of efficient transferring and distribution of heat. In addition, the nanofibers of the heat conductive layer 30 may be capable of prolonged and controlled distribution of heat.

The heat application layer 50 is preferably made from thin and absorbent material so that it may evenly distribute the heat generated by the heat source 10 to the wound bed or injury site and it may absorb the exudates, if any is produced by the wound or injury. As indicated above, the heat application layer 50 may be integrated with the heat conductive layer 30, forming a single layer. Thus, the materials usable for the heat conductive layer 30, as indicated above, may also be utilized for the heat application layer 50.

In addition, the heat application layer 50 may be made from materials such as but not limited to: woven or unwoven fabric, cloth, terrycloth, woven or woven fibers of wool, flax, cotton, and/or yarn, mineral textiles such as but not limited to asbestos, glass and/or fiberglass, and synthetic textile including but not limited to nylon, polyester, and/or acrylic, or any combinations thereof. The heat application layer 50 may have a heat application surface 40, which may be sticky or have a sticky edge to ensure covering or partial covering of the wound, infection or injury. The treatment device 1, in its unused form, may further include a non-sticky layer attached to the heat application surface 40. The non-sticky layer may be removed before use, allowing the treatment device to be securely attached.

In the current embodiments as shown in FIGS. 1, 2 and 3 the heat applicator 20 and heat generating body 70 are both shown as having a rectangular shape. It should be noted that the shape and size of the heat applicator 20 and the heat generating body 70, as well as various components of the treatment device 1, may vary according to the specific design of the device, the need of the user and the wound/infection/injury to be treated. The device and its components may take any shape also due to the extensive use of the current invention such as FIGS. 4A, 4B and 4C.

As indicated below, the device herein disclosed may also utilize in applications that generally require thermal control. For example, the device may be made into pads, strips, or even clothing, in order to satisfy the specific need of the application. The size of the applicator may range from 1 $mm^2$ to 10 $m^2$, with the preferred range of 10 $mm^2$ to 100 $cm^2$. The weight of the treatment device 1 is preferable light, ranging from 0.1 g to 10 kg, and a preferred range of 1 g to 1 kg. The components of the device are preferably removably attached so that each part may be detached from the others and used separately. The applicator portion of the device may be cut or divided into intended size and shape to ensure convenient application.

The current treatment device 1 may be used for any kind of wounds, infections, injuries, and ailments. In addition, the current device may also be used to prevent wound infection by heating a target area prior to, during, or after surgery. The usage doubles to promote normothermia. The treatment device 1 may take the form of operating room padding, garments, coverings, blankets, and the like or any combination thereof. This allows the hospital staff to appropriately maintain/preserve normothermia which is a critical factor of patient stability especially when it comes to resuscitation and treating trauma injuries. Studies have shown that hypothermia can greatly increase the mortality rate of those who require resuscitation or that have experienced great trauma such those wounded in combat. Further, the treatment device 1 can be used to heat or warm intravenous fluids to specific temperatures or ranges of temperatures. By providing a covering for these fluids normothermia can be more easily preserved and the warmed fluids may aid in resuscitation of patients. The fluids can also be pre-warmed, for instances of impending but unknown requirements of use such as a battlefield or trauma unit.

In addition to promoting normothermia, the basic function of the treatment device is to alter the temperature of an external injury site or wound bed to enhance healing and facilitate recovery. In addition, the current treatment device may be used for pain management, mainly by promoting blood flow and improving recovery. The current device may also be used to apply heat treatment for acne and other skin disorders, such as warts, psoriasis, eczema and cancer. In organ transplantation, this device may be used to control and maintain the temperature of the transplant organs during transportation and storage of the transplant organs, as the organs require specific temperature control. The device may additionally be used for internal applications such as the management of cervical conditions and the like.

Those skilled in the art will appreciate that the light and/or heat treatment therapies can be used to treat a range of skin conditions including acne, warts, psoriasis, eczema and cancer as well as many other afflictions. The light or heat treatment may also treat a number of subcutaneous afflictions such as muscle and nerve regeneration, promoting bone healing and managing pain associated with various diseases.

The lighting mechanism 75 is preferably a light emitting nanofiber layer woven into the heat application surface 40. Further, photoluminescent nanofibers may be employed. By taking optical nanofibers and combining them with quantum dots, one can produce a wide spectrum of lighting options and applications. The advantage to using these light emitting nanofibers manifests itself in high efficiency lighting with reduced power consumption. When done correctly, this produces quantum efficiencies in the range of about 0.65 to about 0.95. Additionally, these nanofibers provide flexible lighting options. They can be woven and bent into various shapes and fabrics of varying strengths.

In some embodiments, the lighting mechanism can vary depending on the specific treatment desired. This means the lighting element 75 may be a number of different mechanisms including light emitting diodes (LEDs), lasers, and ultraviolet (UV) light amongst others or any combination thereof. The particular lighting element 75 may change to reflect a specific intended use. Photodynamic therapy (PDT) takes advantage of various light sources to achieve a response. For example, photodynamic medications are activated by a lighting element 75 after a predetermined incubation period. The incubation period varies by the medication, but in any event is the time from which the medicine is ingested or applied until the time the lighting element 75 is applied to the targeted area. Drugs used in such treatments may include Photofrin®, Levulan®, and Metvix® which are used for the treatment of certain cancers.

Additionally, the present invention may be used for photodynamic antimicrobial chemotherapy (PACT). PACT utilizes various photosensitizers and a range of wavelengths of light, typically visible or ultraviolet light, to prompt a phototoxic response. This technique has been shown to be effective against at least bacteria, viruses, yeasts, and parasites in vitro. Thus, PACT presents a cost effective alternative to treating localized infection.

Further, various skin afflictions such as acne can be treated by phototherapy including lasers, LEDs or both. The types of lasers employed by the device for this type of treatment may include Diode, Pulsed Dye, Fractional, KTP, Infrared, and Pulsed Light and Heat Energy (LHE) lasers. In the alternative, the lighting element 75 may consist of a plurality of LEDs affixed or interwoven into the heat application surface 40. The LEDs may also be present in the treatment device 1 itself and shine through one or more layers of the device.

In treating acne, blue wavelength light is typically used for effective treatments. However, the combination of blue wavelength and red wavelength light is sometimes used in conjunction with one another. The duration of the treatment varies between individuals and their particular skin types and conditions, but can range from 10 minutes up to 1 hour.

Additionally, evidence continues to show the involvement of using low level laser therapy (LLLT) as having an application in treating a variety of ailments. The low level light produced by lasers, and in some cases LEDs, is used to alter cellular function. For example, low intensity red light may aid in the inhibition of lesions contributing to diabetic retinopathy. Hence, it may be preferable to appropriately fashion the treatment device 1 that it fits over the eyes of the patient and subjects them to these wavelengths of light. Further applications include, but are not limited to, stroke, traumatic brain injury, Parkinson's disease, Alzheimer's, spinal cord and peripheral nerve injuries. LLLT may be readily optimized and employed by the treatment device 1 through the lighting mechanism 75. LLLT may also be provided by the treatment device 1 by first responders to aid in the treatment of at least the aforementioned afflictions.

Additionally, ultraviolet light may be used to treat certain skin conditions such as psoriasis. Preferably, the UV-B spectrum of light would be used for this purpose. UV-A light can be used for such a treatment, but must be used in conjunction with a light sensitizing medication. Such medications can be taken either topically or orally and will allow the UV-A light to be effective for treatment purposes. If one desired to employ lasers for treating psoriasis, an example might be an Excimer laser or Pulsed Dye laser. Radiofrequency may also be employed for various skin therapies and epilation.

Another practical use of the treatment device 1 combines the heating properties with the use of topical therapeutics such as various types of pain medications or antibiotics. The device 1 may be applied to a particular area in order to increase the uptake of a particular topical drug or antibiotic. The topical drug is applied to the surface of the skin, and then the device 1 can subsequently be applied to the same area. The process is the same if the medication is not topical but rather taken internally. In yet other instances, various therapeutic compounds may be able to be released including nano-based compounds through the thermoregulation process. Such compounds may be applied to the skin surface or directly to the surface of the treatment device 1.

The treatment device 1 in this instance may take any shape as necessary for the intended functionality. There are a number of drugs whose interaction with light can create unwanted side effects including redness, folliculitis, and darkening or lightening of the skin. Thus, in some embodiments, one may desire to use only the heat source 10 and not the light source. These embodiments may provide for a switch or means for turning the light source on or off. By using only the heating source 10 of the device 1, one can avoid any potential side effects of limitations of using the lighting element of the device 1. Again, the treatment device can be formed to fit a number of different bodily structures, which includes but is not limited to masks, bandages, stockings, sleeves, and patches.

The device further can function as a wearable electronic stimulation device. In this instance, the treatment device 1 has electrodes 90 as shown in FIG. 3. The plurality of electrodes 90 are connected to the power supply 60. The electrodes 90 provide a current that can activate nerves or stimulate muscular contractions or have a combined effect on both nerves and muscles (i.e. neuromuscular).

Generally, this form of treatment is known as functional electrical stimulation (FES) or neuromuscular electrical stimulation (NMES). Through this type of therapy, paralyzed or paretic muscles can be forced to contact by subjecting them to electrical currents to the nerves innervating the muscles. Some practical applications include the treatment of foot drop and inducing hand grasping amongst others. The number of electrodes 90 can vary but should be in the range of about 2-15 depending on size and orientation of the electrodes 90 as well as the surface area of the treatment device 1. Preferably there are at least three electrodes 90. The electrodes 90 are those generally used in the stimulation of muscles and nerves. They may be generally discoid in shape although others shapes are readily available. For example, the electrodes 90 can be made to conform to the shape of the treatment device 1 or to that of a particular body part.

Common materials for the electrodes 90 include stainless steel, silver-silver chloride, platinum, and gold plated materials. In some instances, it would be preferential to use flexible electrodes such as carbon filled silicone rubbers or other readily available conductive polymers. Further, the electrodes 90 may exhibit suction like properties that aid in adherence to the body depending on their position relative to the treatment device 1. The electrodes 90 can provide an electrical stimulus in an operating range of about 1 Hertz (Hz) to about 5000 Hz depending on the application. More preferably, the operative range of the electrodes is about 1 Hz to about 200 Hz.

By taking advantage of the inclusion of a number of electrodes 90, the treatment device 1 has a number of practical applications in addition to the numerous applications listed throughout this disclosure and other not yet named. The treatment device 1 can employ the electrodes 90 for pain management as well as nerve regeneration and neurorehabiliation. There is evidence to suggest that this electrical therapy can improve the gait, balance, posture, and motion ranges of the foot and ankle in children with cerebral palsy.

The treatment device 1 may also be used in these applications and others in conjunction with one or more medical devices or monitoring technology. For example, the treatment device 1 may be set to provide a pulsed electronic stimulus of about 100 Hz via the electrode(s) 90. The neuromuscular response may then be recorded and analyzed using various biosensors from the region in question. Additionally, the electrodes 90 can be used to interact with voltage sensitive dyes, known as potentiometric dyes, to plot time versus activity curves and absorb photo emission to produce images and/or transmit data.

The treatment device 1 can be functional as both a research tool and a therapeutic device. In the research setting, the treatment device 1 can help others understand the neural mechanism involved in neuropathic pain conditions such as phantom limb pain, stump pain, post traumatic, neuralgia, post herpetic neuralgia, diabetic mono and poly neuropathy, ischemic neuropathy, and alcohol neuropathy, and the like. Further understanding may be achieved by mapping of the neural pathways involved with some diseases. Such diseases could be targeted by intervention points in the peripheral nervous system (PNS) and central nervous system (CNS). By recording the neural signaling in these systems, various disease states can be treated and identified by bypassing or modifying the neural signal by a number of mechanisms including electrical, thermal, radio frequency (RF), chemical, and pharmaceutical stimuli.

In general the treatment device 1, serves to provide solutions to wound care, injury sites, and skin conditions. The device 1 achieves this through a variety of mechanism including neural excitation which, in turn, leads to vasodilation. Vasodilation is critical to wound healing and subsequently increases the partial pressure of oxygen within the blood. This uptake in oxygen helps to stave off infection through a number of means including oxidative killing. This chain of events is brought upon by an external stimuli including, but not limited to, temperature changes, chemicals, drugs, lighting, and electrical stimulation. Any of a number of these stimuli can provoke an axon reflex mechanism bringing the increase in blood flow to the affected area. A secondary rise in skin blood flow may be mediated by nitric oxide. Nitric oxide is a key component in wound collagen accumulation and a number of cellular functions. All of the above contribute greatly to an increase in the treatment of wounds, injuries, and skin conditions and the present invention uses strategies, including a number of external stimuli, to maximize the effects of such pathways.

In practice the treatment device 1 may be used in a number of different ways and take many different forms as noted above. In some such usage, the treatment device 1 is applied before a patient undergoes a medical procedure, such as an invasive surgery. The treatment device 1 is applied within at least 3 hours of the surgery and in some cases at least 6 hours beforehand. The treatment device should be applied for about 10 minutes to about 2 hours and typically about 30 minutes to about 45 minutes.

After the medical procedure, the treatment device 1 can again be applied to the target area. This application preferably occurs within 3 hours or the procedure and sometimes as long as 4 hours thereafter. The treatment device 1, at this point, is preferably applied for about an hour although it may be as short as 30 minutes and as long as 2 hours. In some instances the treatment may last from about 10 minutes to about 60 minutes. Multiple applications may be required and may be done so at time varying intervals of both the subsequent application time as well as the duration between applications. Typically such an interval is about 1 hour to about 4 hours and is preferably about every 2.5 hours.

Other examples of use may entail for preventive therapies and in trauma settings. For preventive care/therapy it is desirable to apply the treatment device 1 at least twice a day (24 hours) although one application may suffice depending on the severity of the malady to be prevented and duration of use. Each preventative session may last about 30 to 45 minutes and may be as short as 5 minutes and as long as 2 hours. In some instances, the treatment may last for about an hour. Any applications for trauma settings may closely mirror the post-procedural protocol described above, however, the exact duration of application and intervening intervals may be dictated by the type of trauma and the severity. These protocols are intended to be exemplary and other protocols may exist for similar but not named uses. In some instances, function or treatment via the device is suspended while the device is allowed to remain on the patient.

Beside its medical applications, the current device may also be used as other heating platforms, such as but not limited to clothing apparel and accessories including gloves/hand warmers, jackets, pants, socks, shoe insert, ear muffs, footwear such as ski boots, and winter boots, ski equipment, goggles, ice skates, seat pads, portable seat cushions, and heatable containers. A thermal blanket may be used for the treatment of hypothermia and the treatment of cardiac arrest with medically induced hypothermia. As long as the apparatus requires thermal control capability, the current invention may play a central role.

As indicated above, the treatment device may further comprise a control mechanism connected to the power source. The control mechanism may be used to initiate, terminate, and adjust the electricity provided by the power source, thus controlling thermal alternation capability of the device. With the control mechanism, the user of the treatment device may easily control the treatment process and change the durations, cycles, and intensity of the treatments. Additionally, the control mechanism may not be directly connected to the power source. In this instance, the control mechanism is a wireless device capable of communicating with the device 1 itself.

Preferably, a user can employ a Bluetooth® enabled device (i.e. smart phone) to change particular settings such as temperature, cycles, frequency, light intensity and a variety of other functions by way of mobile application or remote center. This embodiment may also allow for the real time monitoring of the device 1 and permit the device 1 to send physiological data to the user (i.e. a doctor) in real time. The data may be able to be stored or interpreted to further manipulate the settings of the treatment device 1. It may be advantageous to use biosensors in the treatment areas to further meet these needs. Alternatively, there may be a system in which the doctor, physician, etc. can selected from preset programming options to provide specific stimuli. In addition stimuli may be altered, changed, or employed based on response to an artificial source or nervous system stimuli including thought generated responses of movement or action.

Additional monitoring may be done with the inclusion of heat sensitive fibers (i.e. fibers that change color in response to temperature). These fibers can be calibrated to have a variety of color outputs over a predetermined temperature range. These fibers can also be sensitive to temperature differentials than less than one degree. Wounds and the surrounding tissue can vary in temperature throughout the healing process, and this visual indicator can help health officials know the progress of the healing while removing expensive existing monitoring technologies. For example, an infection is usually associated with swelling and an increase in temperature. A cutaneous patch, as described in the present invention, with heat sensitive fibers embedded therein would provide a more comprehensive monitoring system and improve patient health and moral.

FIGS. 1, 2, 3, 4A, 4B, 4C and 4D show various embodiments of the current invention. However, it should be noted that the design of the current invention may vary significantly from the embodiments described herein. As long as the general inventive spirit stays consistent with the disclosure, the variations of embodiments should be considered part of the current invention. While some of the variations are hereby described, the other variations may be considered general knowledge to a person skilled in the art so that they do not required detailed discussion. The teachings and disclosures of the current invention encompass all the variations.

What is claimed is:

1. A method of medical treatment comprising the steps of:
providing a medical treatment device, the medical treatment device comprising,
a therapeutic medium,
wherein the therapeutic medium is configured to produce temperatures covering a range of about −10° C. to about 50° C.;
an applicator connected to the therapeutic medium, the applicator comprising,
an application layer having an application surface and a receiving surface with the application layer being configured to be applied to a skin surface of a user, and a conductive layer having a front side and a back side,
wherein the conductive layer is extensively affixed to and completely covers the receiving surface of the application layer;
a plurality of flexible lighting mechanisms being interwoven with fibers of the application layer;
a plurality of flexible electrodes integrated with the application layer;
a power source connected to the therapeutic medium, wherein the power source is at least one battery; and
a wireless transceiver coupled to the power source and configured to provide bidirectional communication between the treatment device and a secondary electronic device,
wherein patient information is sent in real time from the treatment device to the secondary electronic device;
applying the medical treatment device to at least one patient for a predetermined time frame before the at least one patient undergoes at least one medical procedure.

2. The method of claim 1 wherein the medical treatment device is applied at least two hours before the at least one patient undergoes the at least one medical procedure.

3. The method of claim 1 wherein the predetermined time frame is about 10 minutes to about 60 minutes.

4. The method of claim 1 further comprising the step of:
adjusting an output temperature of the medical treatment device during the predetermined time frame.

5. The method of claim 1 further comprising the step of:
suspending operation of the medical treatment device while retaining the medical treatment device on the at least one patient.

6. The method of claim 1 further comprising the step of:
removing the medical treatment device from the at least one patient at the end of the predetermined time frame.

7. The method of claim 1 wherein the medical treatment device is applied to a skin surface of the at least one patient.

8. The method of claim 1 further comprising the steps of:
applying or activating the medical treatment device to the at least one patient after the at least one patient has undergone at least one medical procedure for a second predetermined time frame.

9. The method of claim 8 further comprising the step of:
applying the medical treatment device to the at least one patient for at least one subsequent timed interval,
wherein each subsequent timed interval is the same or different in duration as any other timed interval.

10. The method of claim 8 wherein the medical treatment device is applied within about 4 hours of the at least one medical procedure.

11. The method of claim 8 wherein the second predetermined time interval is about 30 minutes to about 2 hours.

12. The method of claim 9 wherein each interval is about 2 hours and 30 minutes.

13. The method of claim 1 wherein the medical treatment device is a cutaneous patch which can be applied to any bodily surface.

14. The method of claim 1 wherein the medical treatment device is used in a treatment protocol comprising nanoparticles.

15. The method of claim 1 wherein the predetermined time frame is about 30 minutes to about 45 minutes.

16. A method of medical treatment comprising the steps of:
providing a medical treatment device, the medical treatment device comprising,
a therapeutic medium,
wherein the therapeutic medium is configured to produce temperatures covering a range of about −10° C. to about 50° C.;
an applicator connected to the therapeutic medium, the applicator comprising,
an application layer having an application surface and a receiving surface with the application layer being configured to be applied to a skin surface of a user, and a conductive layer having a front side and a back side,
wherein the conductive layer is extensively affixed to and completely covers the receiving surface of the application layer;
a plurality of flexible lighting mechanisms being interwoven with fibers of the application layer;
a plurality of flexible electrodes integrated with the application layer;
a power source connected to the therapeutic medium, wherein the power source includes at least one of a battery, an electrical power source, a chemical power source, or a combination thereof; and
a wireless transceiver coupled to the power source and configured to provide bidirectional communication between the treatment device and a secondary electronic device,
wherein patient information is sent in real time from the treatment device to the secondary electronic device;
applying the medical treatment device to at least one patient for a predetermined time frame before the at least one patient undergoes at least one medical procedure;
applying the medical treatment device to the at least one patient after the at least one patient has undergone at least one medical procedure for a second predetermined time frame; and
applying the medical treatment device to the at least one patient for at least one subsequent timed interval,
wherein each subsequent timed interval is the same or different in duration as any other timed interval.

17. A method of preventive medical care comprising the steps of:

providing a medical treatment device, the medical treatment device comprising,
   a therapeutic medium,
      wherein the therapeutic medium is configured to produce temperatures covering a range of about −10° C. to about 50° C.;
   an applicator connected to the therapeutic medium, the applicator comprising,
      an application layer having an application surface and a receiving surface with the application layer being configured to be applied to a skin surface of a user, and a conductive layer having a front side and a back side,
         wherein the conductive layer is extensively affixed to and completely covers the receiving surface of the application layer;
   a plurality of flexible lighting mechanisms being interwoven with fibers of the application layer;
   a plurality of flexible electrodes integrated with the application layer;
   a power source connected to the therapeutic medium,
      wherein the power source is at least one of a battery, an electrical power source, a chemical power source, or a combination thereof; and
   a wireless transceiver coupled to the power source and configured to provide bidirectional communication between the treatment device and a secondary electronic device,
      wherein patient information is sent in real time from the treatment device to the secondary electronic device;
applying the medical treatment device to at least one user for a predetermined time frame,
   wherein the medical treatment device is applied at least twice within a 24 hour time frame, with each application being the same or different in duration.

18. The method of claim 17 wherein the duration of application is about 15 minutes to about 2 hours.

19. The method of claim 18 wherein the duration of application is about 1 hour.

20. The method of claim 17 wherein a duration between applications of the medical treatment device is about 2 hours and 30 minutes.

21. The method of claim 17 wherein the medical treatment device is a stocking covering at least a portion of a leg and toes or arms and fingers of the user or a covering for a head region of the user.

22. A method of medical treatment comprising the steps of:
providing a medical treatment device, the medical treatment device comprising,
   a therapeutic medium,
      wherein the therapeutic medium is configured to produce temperatures covering a range of about −10° C. to about 50° C.;
   an applicator connected to the therapeutic medium, the applicator comprising,
      an application layer having an application surface and a receiving surface with the application layer being configured to be applied to a skin surface of a user, and a conductive layer having a front side and a back side,
         wherein the conductive layer is extensively affixed to and completely covers the receiving surface of the application layer;
   a plurality of flexible lighting mechanisms being interwoven with fibers of the application layer;
   a plurality of flexible electrodes integrated with the application layer;
   a power source connected to the therapeutic medium,
      wherein the power source is at least one battery; and
   a wireless transceiver coupled to the power source and configured to provide bidirectional communication between the treatment device and a secondary electronic device,
      wherein patient information is sent in real time from the treatment device to the secondary electronic device;
applying the medical treatment device to at least one patient for a predetermined time frame before, during, or after, or any combination thereof, the at least one patient undergoes at least one medical procedure.

\* \* \* \* \*